United States Patent
Alving et al.

(10) Patent No.: US 6,626,844 B1
(45) Date of Patent: Sep. 30, 2003

(54) METHOD AND COMPOSITION FOR INHIBITION OF NITRIC OXIDE PRODUCTION IN THE ORAL CAVITY

(75) Inventors: Kjell Alving, Uppsala (SE); Jon Lundberg, Stockholm (SE)

(73) Assignee: Aerocrine AB, Solna (SE)

( * ) Notice: Subject to any disclaimer, the term of this patent is extended or adjusted under 35 U.S.C. 154(b) by 0 days.

(21) Appl. No.: 09/601,289

(22) PCT Filed: Jan. 29, 1999

(86) PCT No.: PCT/SE99/00123
§ 371 (c)(1),
(2), (4) Date: Sep. 1, 2000

(87) PCT Pub. No.: WO99/39199
PCT Pub. Date: Aug. 5, 1999

(30) Foreign Application Priority Data

Jan. 30, 1998  (SE) ................................................ 9800273

(51) Int. Cl.[7] .................................................. A61B 5/00
(52) U.S. Cl. ........................... 600/532; 73/23.3; 422/84
(58) Field of Search .......................... 600/532; 73/23.3; 422/84

(56) References Cited

U.S. PATENT DOCUMENTS

| 4,060,600 A | 11/1977 | Vit |
| 4,406,810 A | 9/1983 | Boden |
| 5,602,150 A | * 2/1997 | Lidsky ........................ 514/327 |
| 6,010,459 A | * 1/2000 | Silkoff et al. ................ 600/532 |
| 6,038,913 A | * 3/2000 | Gustafsson et al. ......... 600/532 |
| 6,043,268 A | * 3/2000 | Maeda et al. ................ 514/401 |

FOREIGN PATENT DOCUMENTS

| GB | 2299263 | 10/1996 |
| WO | WO9316681 | 9/1993 |

OTHER PUBLICATIONS

Dialog Abstract, accession No. 08650695 of Nat. Med. 1(6):546–551 (1995) (abstract only).

Dialog Abstract, accession No. 10632680 of Chest 110(4):930–938 (1996) (abstract only).

Dialog Abstract, accession No. 01097389 of Comparative Biochemistry and Physiology A 118(4):939–948 (1997) (abstract only).

* cited by examiner

Primary Examiner—Robert L. Nasser
(74) Attorney, Agent, or Firm—Dinsmore & Shohl LLP

(57) ABSTRACT

The disturbing influence or orally produced nitric oxide in the measuring of exhaled nitric oxide can be ameliorated or totally eliminated through the use of a method and composition according to the present invention. The production of NO in the oral cavity is temporarily inhibited by the application of a composition having anti-bacterial and/or pH increasing effect.

9 Claims, 5 Drawing Sheets

Figure 1:
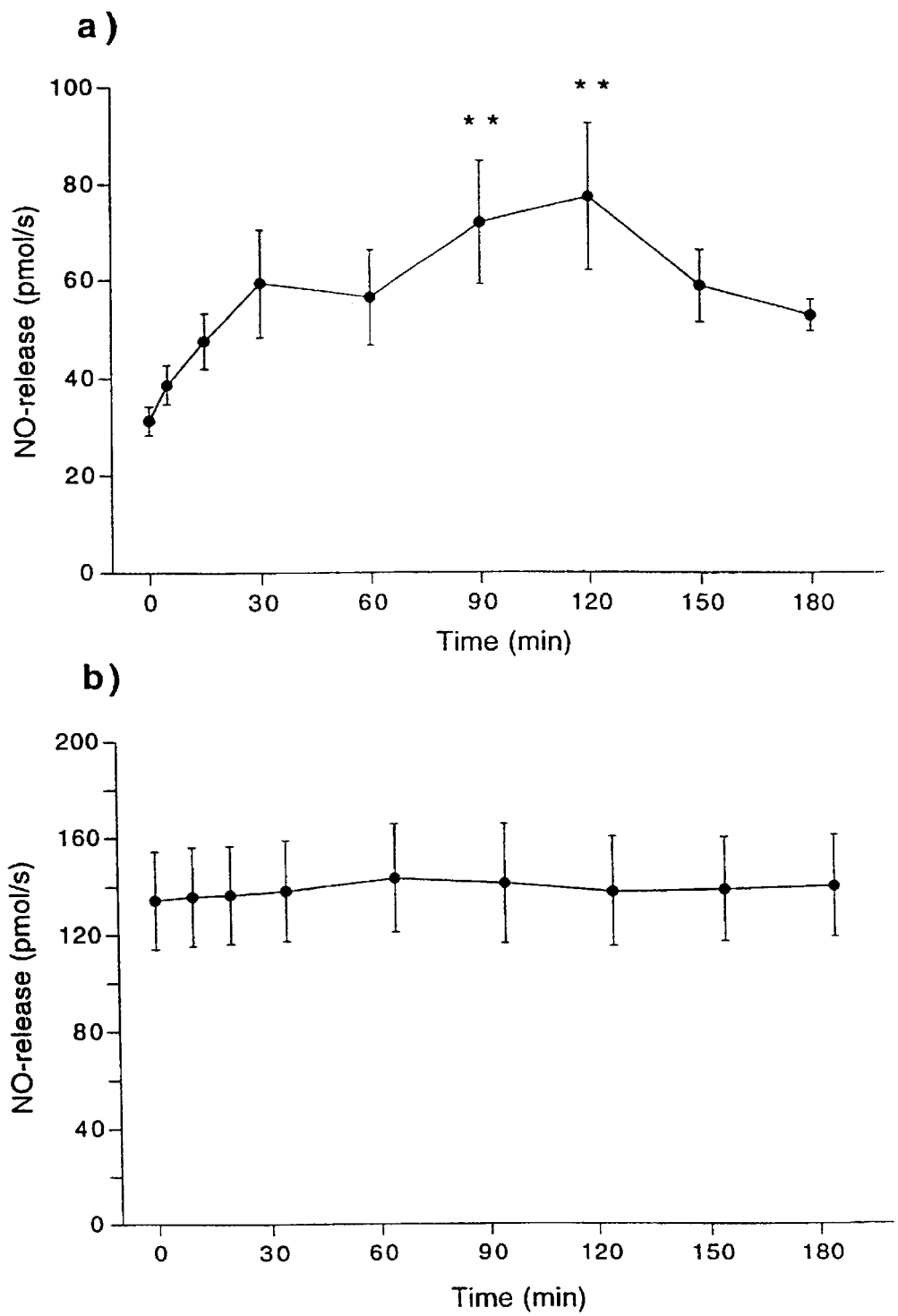

METHOD AND COMPOSITION FOR INHIBITION OF NITRIC OXIDE PRODUCTION IN THE ORAL CAVITY

The present invention concerns the field of diagnostic measurement of nitric oxide in orally exhaled air and in particular how to avoid the influence of nitric oxide produced in the oral cavity in these measurements. Consequently, a composition, method and device for this purpose are disclosed.

BACKGROUND OF THE INVENTION

It has been shown that increased NO levels in the orally exhaled breathing air is an indication of an inflammatory condition in the airways. A system and method for the determination of NO levels in orally exhaled air for diagnosis of inflammatory conditions is described, for example in WO 95/02181; Alving, K. et al. and WO 93/05709; Gustafsson, L. E.

Nitric oxide is normally produced enzymatically by constitutive NO synthases in, e.g. nerves and endothelial cells; these enzymes yield the relatively small amounts of NO involved in physiological regulation of nerve transmission and vascular tone. In contrast, the inducible NO synthase found, e.g. in activated white blood cells and airway epithelium produces NO at a high rate. It was recently shown that nitric oxide is also produced through a second route, i.e. through reduction of nitrite. Nitrite is present in body fluids such as saliva and urine, in amounts depending on the individual's diet and health. For example, a diet rich in nitrate (such as certain vegetables) will result in high nitrate levels in saliva and urine. The bacteria normally present in the oral cavity will reduce salivary nitrate to nitrite.

The oral cavity or cavum oris is generally considered to comprise the cavity from the lips to epiglottis and this definition will be applied in the following description.

Further reduction of salivary nitrite to nitric oxide occurs normally in the acidic and reducing environment of the stomach (Lundberg et al. 1994, Gut, 35:1543–46). It is worth noting, that saliva contains relatively high amounts of ascorbic acid, the reducing capacity of which will enhance the production of NO from nitrite. Levels encountered in orally exhaled air can be in the interval of 30 to 50 pmol/s for healthy subjects and about 60 to 100 pmol/s for asthmatic patients. In healthy persons, the ingestion of nitrate rich food and the NO synthesis in the oral cavity may under certain conditions result in levels in the order of magnitude of 70 pmol/s. This is clearly in the asthmatic range, which makes this a potential source of error and misinterpretation of the results.

In Nature Medicine, vol. 1, no. 6, June 1995, Duncan et al. report their studies of nitric oxide generation in the oral cavity including experiments, where healthy volunteers have used an antibacterial mouthwash and an ascorbic acid mouthwash. Prior treatment with ascorbic acid caused an marked elevation in NO production and an initial reduction in salivary nitrite concentration. Conversely, prior treatment with antiseptic mouthwash (Eludril®) caused an initial reduction in NO production and a reduced salivary nitrite production. The results indicate, that NO synthesis was inhibited by 36±10%. The authors are however focused on showing the beneficial effects of NO production and have not addressed the problems associated with this in relation to diagnostic measurements.

Surprisingly, the contribution of NO from the oral cavity may, under certain circumstances, be high enough to cause errors in diagnostic measurements, e.g. measurements according to WO 95/02181; Alving, K. et al. or WO 93/05709; Gustafsson, L. E. The consequences may be that a healthy person exhibits NO values corresponding to values of a person having asthma and an asthmatic, showing increased values may run the risk of being prescribed unnecessarily high doses of steroids or other anti-inflammatory medication. Obviously, with the development of this new concept of detection and diagnosis, which presently gains wider acceptance, there is an evident need for a reliable method and/or a safe composition which eliminates this possible source of error.

SUMMARY OF THE INVENTION

The present invention discloses a method and composition according to the attached claims, which for the first time substantially reduces or eliminates the possible source of error due to orally produced NO when measuring orally exhaled NO, and furthermore, does so in a practical, easy and reproducible way.

SHORT DESCRIPTION OF THE DRAWINGS

The invention will be described in closer detail in the following, with reference to examples and attached drawings, in which FIG. 1 shows NO measurements after nitrate intake. a) Increase of NO in exhaled air, registered as NO release rate (pmol/s) during the plateau of a single-breath exhalation, after ingestion of 400 mg potassium nitrate. b) Nasal NO release rate obtained by sampling air (0.5 L/min) from the nose in the same experiment. Values are expressed as mean±SEM (n=10).

Figure 2:
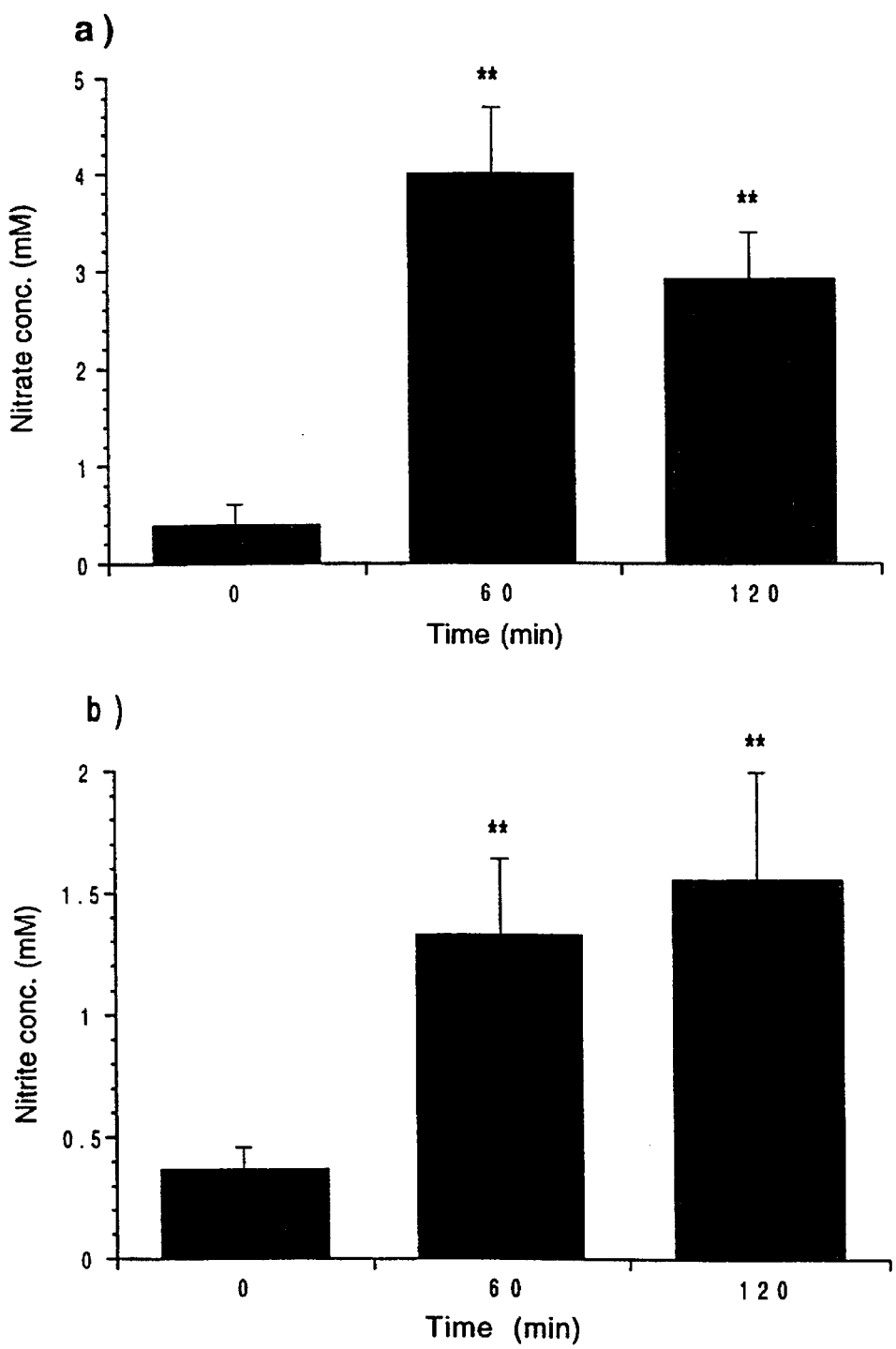

FIG. 2 shows a) Nitrate and b) nitrite concentration in the saliva after nitrate loading: Samples were collected immediately before, and 60 and 120 min after ingestion of 400 mg potassium nitrate. Values are expressed as mean±SEM (n=7).

Figure 3:
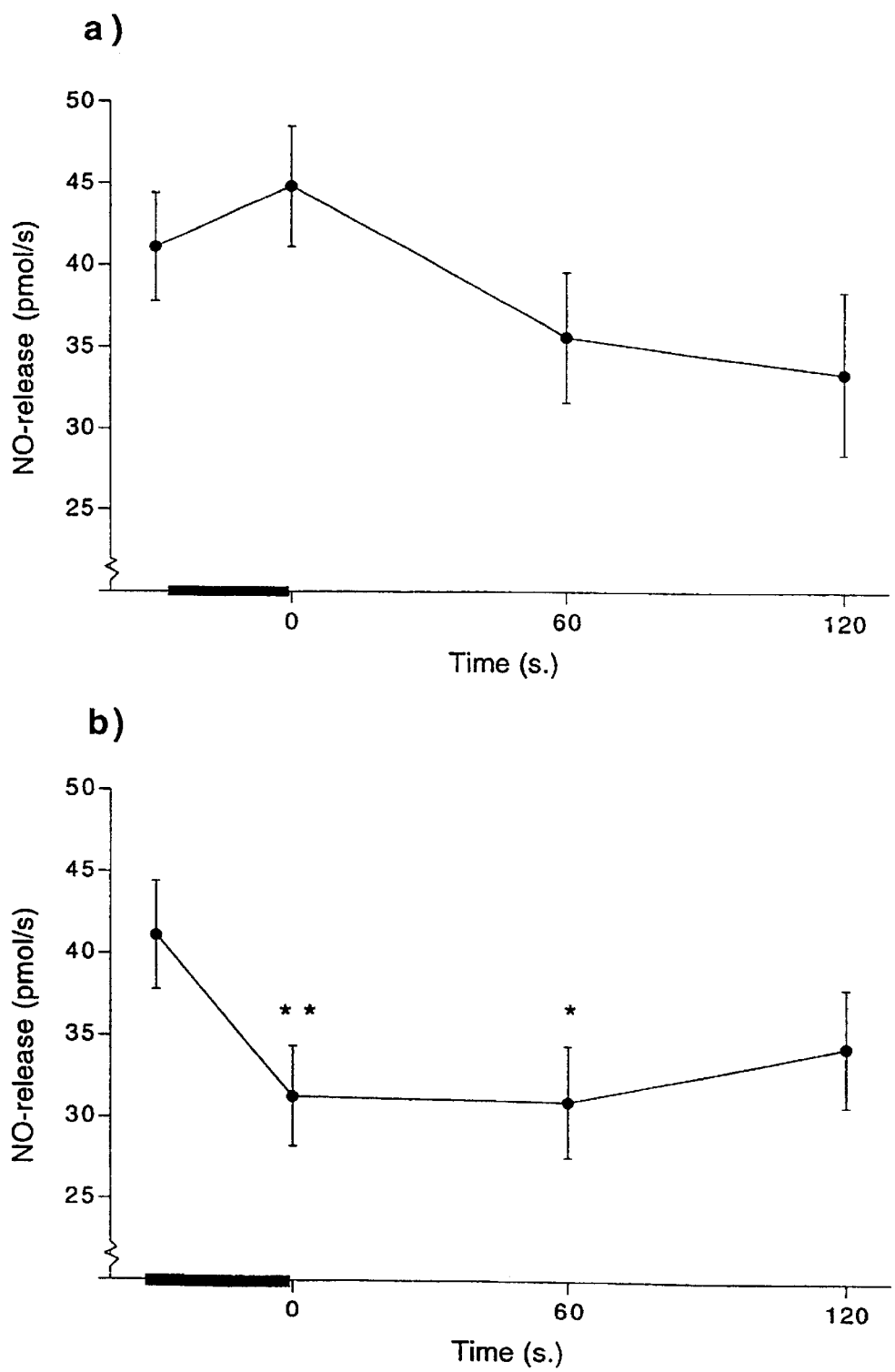

FIG. 3 shows the effects of mouthwash with a) distilled water and b) sodium bicarbonate (10%) on the NO release rate. The thick bar on the time scale represents the 30 sec mouthwash period. Values are expressed as mean±SEM (n=10).

Figure 4:
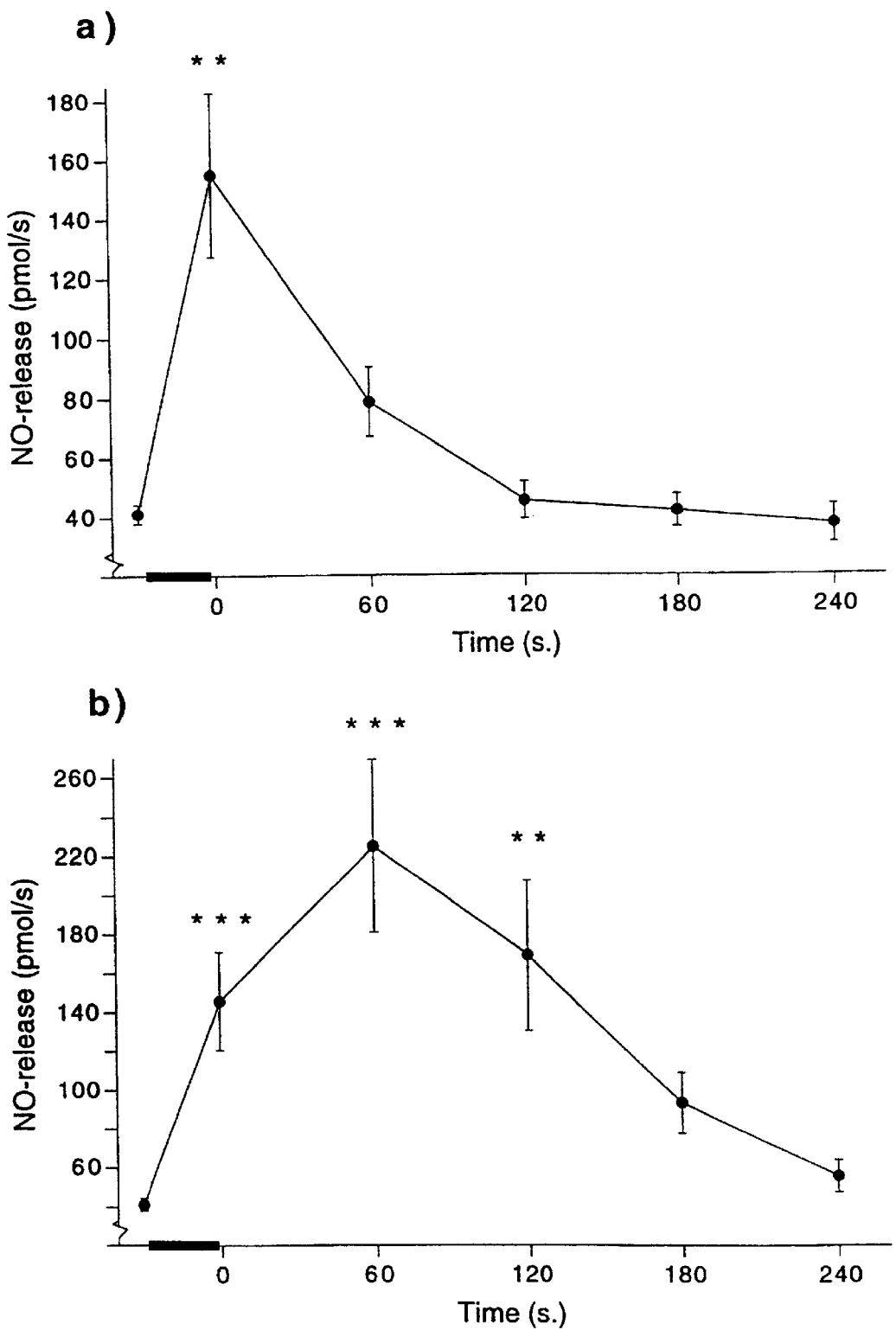

FIG. 4 shows the increased NO release into exhaled air after mouthwash with a) ascorbic acid (3%) and b) 10 mM potassium nitrite. The thick bar on the time scale represents the 30 sec mouthwash period. Values are expressed as mean±SEM (n=10).

Figure 5:
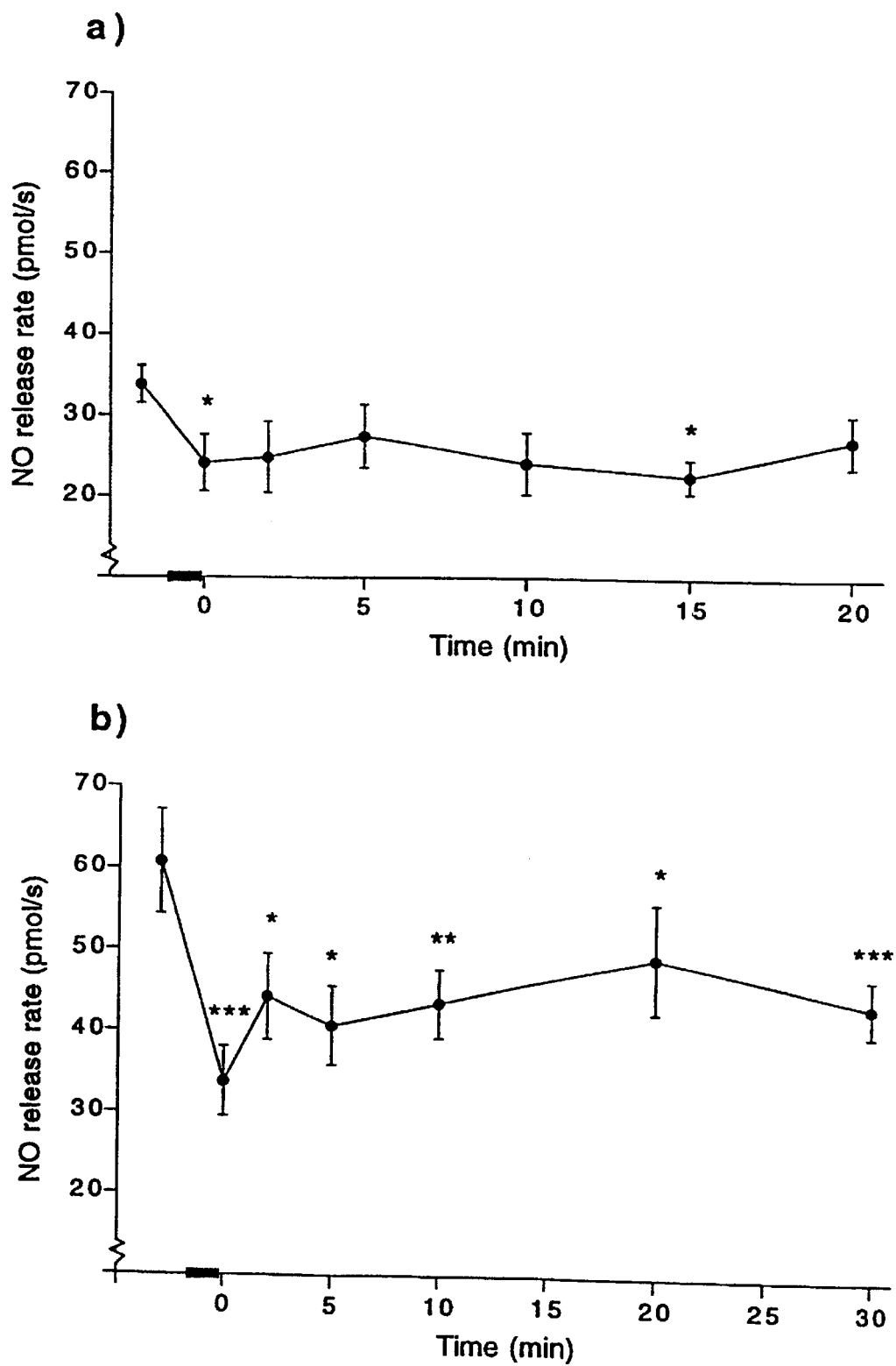

FIG. 5 shows the effects on exhaled NO by mouthwash with chlorhexidine acetate (0.2%). a) Decrease of NO release in orally exhaled air after chlorhexidine rinsing in control (fasting) situation. b) Subjects pre-treated with 400 mg potassium nitrate 90 min before baseline measurement and the subsequent mouthwash. The thick bar on the time scale represents the 30 sec mouthwash period. Values are expressed as mean±SEM (n=10).

DESCRIPTION OF THE INVENTION

The present invention for the first time makes available a method in the diagnostic determination of orally exhaled nitric oxide (NO) in humans, where the production of NO in the oral cavity may constitute a disturbance on the measurement of the level of NO, characterized in that said NO production in the oral cavity is temporarily inhibited through influencing the prerequisites for NO formation, in particular non-enzymatic NO formation in the oral cavity, for example by local administration of a composition that changes said prerequisites prior to said measurement.

The expression "temporarily inhibited" means that the NO production is influenced in a reversible manner, i.e. that a normal NO production will resume after a time period allowing for an undisturbed NO measurement to be made. In this context it is to be noted, that the normal production of NO in the oral cavity in general is beneficial. The inventive method is not aimed at permanently eliminating this function.

The expression "local administration" means that a composition is brought in contact with all surfaces in the oral cavity, i.e. the cavity between the lips and epiglottis, including the teeth, gums, tongue and palate.

The expression "brought in contact with" comprises rinsing (e.g. gargling), painting, spraying and brushing the composition on said surfaces. The administration of the composition can be performed by or in conjunction with mechanical cleaning of the oral cavity, e.g. brushing. In this context, it is to be noted that as the tongue is covered with papillae, it may be difficult to reach the bacteria taking part in the NO production. It is therefore suggested that also the surface of the tongue is cleaned, e.g. brushed or scraped. The possibility of using substances which open or dilate the crypts, harbouring bacteria, is also contemplated within the scope of the present invention.

The NO produced in the oral cavity can originate from different pathways. The major source is believed to be salivary nitrate, being reduced to nitrite and further to nitric oxide by nitrate and nitrite reductases of bacterial origin. Additionally, the acidic environment and the presence of reducing substances, such as ascorbic acid, in saliva, promotes the production of NO. The presence of bacteria with the ability of NO production cannot be ruled out. Most bacteria capable of nitrate reduction also synthezise the nitrate reductase enzyme in an anaerobic environment and nitrate reduction is thus rapidly decreased in the presence of oxygen. In this way substances that release oxygen, e.g. hydrogen peroxide or sodium carbonate may inhibit nitrate reduction. Further, the presence of inducible nitric oxide synthase (iNOS) has been shown in human gingival tissue.

Consequently, the production of NO in the oral cavity can be influenced in many ways, including the removal of saliva, for example by rinsing the mouth with sterile water or a suitable mouthwash, the use of bacteriostatic or bacteriocidic substances, increasing the pH above neutral or preferably above pH 8, specific inhibition of bacteria that play a central role in NO production, general removal of bacteria, and/or neutralization of ascorbic acid e.g. using ascorbate oxidase. Another agent, which may oxidise ascorbic acid is podium carbonate. This reaction may be catalyzed by copper sulphate. As human gingival tissue samples have been shown to contain iNOS, there is possibly also an enzymatic source of NO. The activity of this enzyme can be blocked by administering an unselective NO synthase inhibitor such as N-omega-nitro-L-arginine methyl ester or an iNOS-selective inhibitor such as aminoguanidine. Obviously, a combination of two and more of the above approaches is possible.

The pH optimum for bacterial nitrate reductase is around pH 8. Therefore, an advantage of increasing salivary pH above 8 would be, besides inhibiting chemical NO production from nitrite, to inhibit nitrate reductase activity.

Thus, one embodiment of the invention comprises a method for use in conjunction with the diagnostic determination of orally exhaled nitric oxide (NO) in humans, where the production or synthesis of NO in the oral cavity may constitute a disturbance on the measurement of the level of NO, characterized in that the bacterial activity in the oral cavity is temporarily inhibited through mechanical cleaning of the teeth, gums and tongue, together with local administration of an anti-bacterial composition prior to the measurement of orally exhaled NO.

An "anti-bacterial" composition means a composition comprising an agent, capable of temporarily inhibiting or arresting the bacterial activity in the oral cavity. Anti-bacterial agents, approved for local use in the oral cavity, are well known. Examples (concentration, upper limit) include chlorhexidine (0.5%), phenethanol (0.5%), chlorobutol (0.5%), propagine (0.02%), methagine (0.2%), benzyl alcohol (2%), benzalcon chloride (0.02% often i combination with 0.1% EDTA), chloro cresol (0.3%), sodium bensoate (0.1%), hydrogen peroxide, hydrogen peroxide forming compositions, xylitol, iodine and chlorine based compositions. When selecting a suitable agent, the chemistry of NO production must be taken into account. For example $O_2$, released during rinsing with peroxide, may influence the facultatively anaerobic bacteria and provoke the onset of aerobic metabolism. Other compounds, such as iodine, can influence the chemical reduction of nitrite to NO. Further, when choosing an anti-bacterial agent and its concentration, consideration has to be given to possible irritating properties, unpleasant taste etc. The invention is not limited to the above examples as the choice of a suitable anti-bacterial agent involves no inventive effort of a person skilled in the art.

In a farther embodiment of the invention the method includes the simultaneous administration of an oxidizing agent or, preferably, that the anti-bacterial composition includes an oxidizing agent. Further, the anti-bacterial composition preferably includes an oxidizing agent and that the composition is capable of increasing the pH of the saliva to neutral or preferably basic pH, e.g. above 8.

Further, the composition according to the invention can comprise specific nitrate reductase inhibitors, thus influencing the enzymatic part of the NO synthesis taking place in the oral cavity. Co-factors for the nitrate reductase include e.g. a molybden/pterin complex and accessory redox groups $Fe_4S_4$ and heme-b. These co-factors are potential targets for nitrate reductase inhibition.

Further, the composition according to the invention can consist of an aqueous bicarbonate solution, such as sodium bicarbonate, preferably an aqueous sodium bicarbonate solution buffered to a pH of about 8. Suitable buffers include, but are not limited to, organic buffers such as Trometamol® or trishydroxy methyl amino methane.

Additionally, the above buffered aqueous sodium bicarbonate solution preferably comprises a suitable surfactant, such as polyoxyethylene sorbitan monolaurate, for example Tween-20®, sodium dodecyl sulphate and sodium stearate. Also compounds such as ethanol and diethyl ether can be used. A suitable surfactant can be chosen among both ionic and non-ionic surfactants. Finally, the composition can comprise suitable flavourings, coloring agents, and bulk agents to give the product the desired taste, appearance, texture and mouthfeel.

The mode of administration of a suitable composition according to the present invention can be rinsing or gargling, such as the use of a mouthwash, spraying or brushing. Additionally, the composition can be administered in the form of a lozenge, allowed to dissolve in the mouth.

Further, according to one embodiment the composition is administered in the form of a gel or paste with the aid of a brush. In this manner, both a mechanical cleaning and an even distribution of the composition is achieved.

Most preferred by the inventors is a method wherein the composition is administered in the form of a gargling solution, which is kept agitated in the mouth sufficiently long for the active ingredients to exert their influence. Preferably about 10 ml or more of the solution is taken in the mouth and agitated for at least one minute.

The present invention also comprises a composition for inhibiting or preventing non-enzymatic and/or enzymatic NO production in the oral cavity, for example an anti-bacterial composition for inhibiting or neutralising the bacterial activity in the oral cavity prior to diagnostic determination of orally exhaled nitric oxide, characterized in that said anti-bacterial composition includes an oxidizing agent. The expression "anti-bacterial composition" means, that the composition in itself comprises an anti-bacterial agent. Examples of such agents, commercially available, has been given above. As described above, it is also preferred, that the composition, when administered to the oral cavity, increases the pH of the saliva to a level to about or above pH 8.

According to one embodiment of the invention, the composition for inhibiting the production of in the oral cavity prior to diagnostic determination of orally exhaled nitric oxide, is formulated as a gargling solution. In a preferred embodiment of the invention, this gargling solution consists of an aqueous bicarbonate solution buffered to a pH of about 8 and containing an effective amount of a surfactant, suitable for the purpose and generally recognised as safe (GRAS).

According to another embodiment, the composition for inhibiting or neutralising the production of NO in the oral cavity prior to diagnostic determination of orally exhaled nitric oxide, is formulated as a paste or gel. Other suitable formulations or modes of administrations include tablets or lozenges that dissolve in the mouth, chewable compositions, e.g. compositions with a gum base such as gum Tragacanth.

According to still another embodiment, the composition according to the invention is a liquid, which can be sprayed or nebulized into the mouth. Obviously, also a fine, particulate powder can be nebulized into the mouth.

Preferably, the invention comprises a device for use in inhibiting the production of NO in the oral cavity prior to diagnostic determination of orally exhaled nitric oxide, characterized in that said device comprises a composition as specified in the description of embodiments of the invention in the form of a paste or gel and a brush. A specially preferred embodiment of the invention is a device for inhibiting or neutralising the bacterial activity in the oral cavity prior to and during diagnostic determination of orally exhaled nitric oxide, characterized in that said device comprises the composition in the form of a paste or gel, pre-dispensed on a brush. Optionally, the brush can be supplied with an indicator, such as a heat sensitive indicator, a pH indicator or a nitrite/nitrate sensitive indicator, the color change of which indicates when a sufficient cleaning has been performed.

EXAMPLES

Ten healthy non-smoking subjects, age 23–43, were included in the study. The NO measurements were made with a chemiluminescense technique according to the recommendations recently described in the ERS Task Force Report (Kharitonov et al., 1997). The values of NO concentration were then registered in a computer software program together with the values of flow and pressure, measured with a pneunotachygraf, and calculations of these parameters were presented on a screen.

The following describes briefly the "single-breath" method for orally exhaled air. Compressed NO free air was continuously flowing into a non-diffusing gas collection bag, 100 l capacity (Hans Rudolph Inc.), at a rate of 2–3 l/min. The bag was connected via a tube to a Y-piece with a one-way valve, which in turn was adapted to a mouthpiece. Before the measurements the subjects inhaled NO free air through the mouthpiece and were asked to hold their breath for 10 s while they put their tongue into the mouthpiece's opening, in order to prevent NO from diffusing out. Then the subjects exhaled through the mouthpiece at a flow rate of about 0.15 l/s against a resistance of 50 $cmH_2O/l/s$ (Hans Rudolph Inc.), giving rise to an oral pressure of 8–10 $cmH_2O$, for a period of 20 s. The exhaled air went out through the other one-way valve in the Y-piece leading on to a linear pneumotachymeter (Hans Rudolph Inc.), where the values of flow and pressure were registered and transformed into digital signals recorded by a computer software program (Medical Breath Analyser™ from Aerocrine AB, Sweden). The recordings were instantly visualized on a computer screen, which enabled the subjects to maintain a certain flow (i.e. 0.15 l/s), adjusting the exhalation to the flow curve. A fraction of the exhaled air was aspirated into the NO analyzer (Eco Physics Inc., Model CLD 700 AL) at a flow rate of approximately 0.5 l/min, through a 110-cm narrow-bore and Teflon®-coated tube connected to the mouthpiece. The detected NO levels were passed on to the computer and integrated with the figures for flow and pressure for calculation of NO release rate (pmol/s) and NO amount (pmol). NO release was calculated by the formula: NO-conc×Q=pmol/s×l/s=pmol/s. The conversion of NO-conc in ppb to a molecular unit goes via the fact that the volume of 1 mol of NO takes up 24.445 liters at normal temperature and pressure. Given this 1 ppb NO equals 40.908 pM. At the flow of 0.15 l/s and e.g. a NO-conc of 10 ppb the NO release equals 67 pmol/s. The use of NO-release, instead of NO-concentration as a registration unit, has the advantage of taking the flow rate into account, whereas in the use of NO-concentration the exhalation flow is not taken into consideration. In addition to the curves for flow and pressure two curves for NO concentration and NO release were plotted on the screen and calculated mean values were presented for the last 40% of the breath, representing the plateau phase. NO amount was also presented for the first 40%, representing the area under curve for the peak.

In the series of measurements after the nitrate ingestion the subjects were asked to make one single-breath exhalation without a breathhold at every point of measurement, as well as one with as described above. But apart from the difference in breathhold the procedure was exactly the same.

To look into nasal NO levels a somewhat new approach taking advantage of the set-up for measurements in exhaled air was used. A "nose-olive", tried out individually for a tight fitting to the subject's nostrils, was attached to the Teflon®-coated tube leading in to the NO-analyzer. The olive was then placed in one of the nostrils letting the NO analyzer aspirate air from the nasal cavity. Even though the subjects kept breathing through their mouth the NO concentrations oscillated with every breath, pointing to a leakage of NO from the nose to the oral cavity. The subjects were asked to take a deep breath and exhale through the mouthpiece against the same resistance as above, while the olive still was sampling from the nose. The oscillations of the NO values then ceased and the concentrations increased to a stable plateau, visualized on the computer screen. The time for exhalation was set to 20 s. which was well sufficient to reach a plateau. A mean value of the NO concentration during the last 40% of the exhalation, i.e. 8 s. was presented by the computer program and included in the protocol. After a completed measurement in one nostril the olive was moved to the other nostril and the procedure was repeated. In the following calculations the mean value of the concentrations obtained from both of the nostrils from the two observations for every time point were used.

Changes in NO levels were analysed by using non-parametric ANOVA for paired and repeated measures with subsequent Dunn's post-test as offered by InStat from GraphPad Software. Nitrate and nitrite concentrations in the saliva were analysed by the non-parametric method of Mann-Whitney for paired measurements, using the same software.

Example 1

Nitrate Loading

The ten subjects had been fasting over night and the experiments were performed in the morning. Baseline values of NO in exhaled air and from the nasal cavity were collected before the ingestion of nitrite. Three single-breaths with and without a breathhold were performed to obtain a median value for each procedure. The measurements from the nasal cavity proved to be more consistent from time to time, so one measurement from each nostril was held sufficient to get a baseline. A sample of saliva was also taken at this point to get an initial value of the nitrate and nitrite concentration. The subjects chewed on a small piece of Teflon®-plastic for 1 min and the saliva produced were put in tubes and stowed away in the freezer for later analysis. New samples of saliva were collected 60 and 120 min after the nitrate ingestion. The analyses of saliva were eventually limited to the samples from 7 subjects.

An amount of 400 mg potassium nitrate was dissolved in a cup of distilled water and then swallowed down. This nitrate load is equivalent to e.g. 140 g of head lettuce or 200 g of spinach. The subjects were asked to rinse their mouth with tap water after the ingestion. NO measurements in exhaled air and from both of the nostrils were then performed consecutively during a period of 3 hours. The time points were set to 5, 15, 30, 60, 90, 120, 150 and 180 minutes. NO in exhaled air was measured first without and then with a breathhold, as mentioned above.

The experiment was terminated with a mouthwash of sodium bicarbonate after 180 min with a following single-breath measurements. This to examine whether the mouthwash's possible reduction of the NO formation would be enhanced at a stage when one would expect high levels of NO. For mouthwash procedure see below.

Exhaled levels of NO increased steadily after the nitrate ingestion with a maximum after 120 min. The NO release during the plateau had then increased with almost 150% (FIG. 1$a$) compared to baseline (77.0±15.2 vs 31.2±3.0 pmol/s, $p<0.005$), when the procedure without a breathhold was used. The results of the plateau measurements done with a breathhold was used. The results of the plateau measurements done with a breathhold were very similar at every time point and even here a peak of NO release was observed after 120 min (70.8±11.6 vs 31.9±4.5 pmol/s, $p<0.005$). At no time point there was any significant difference between the two procedures (p-value ranging from 0.19–1.00), regarding the plateau levels.

The peak levels of NO, obtained after breathhold, were also elevated to a maximum after 120 min. The NO values, here given as total amount NO released during the first 40 % of the exhalation, went up with 130% compared to baseline (358.3±25.2 vs 819±160.8 pmol, $p<0.005$).

The nitrate concentration in saliva showed a 10-fold increase 60 min after the nitrate ingestion (4.00±0.69 vs 0.40±0.21 mM, $p<0.05$). At 120 min the levels were somewhat reduced (2.92±0.48 mM, $p<0.05$). The nitrite concentration, on the other hand, did not reach it's peak until 120 min after the nitrate load (1.56±0.44 vs 0.37±0.09 mM, $p<0.05$), thus a parallel time-lapse to the increase of NO in exhaled air. There was a trend towards statistical correlation between NO-levels and nitrite concentrations, but it never turned out truly significant.

Regarding the nose no significant changes in NO production were found during the 3 hours followed upon the nitrate loading ($p<0.05$, 5–180 min) (FIG. 1$b$).

Example 2

NO Formation From Saliva in Vitro

On another occasion the subjects were asked to produce 10 ml of saliva, without time restriction, by again chewing on a piece of Teflon®-plastic. Half of this, i.e. 5 ml, was put in a 50 ml plastic syringe with an addition of 0.5 ml distilled water and closed with a three-way stopcock after filling it up with 50 ml of room air. The remaining 5 ml were mixed with 0.5 ml 20 mM nitrite solution (resulting in a salivary nitrite concentration of a bit more than 2 mM) and put in another syringe filled with 50 ml of room air. The two syringes were put in a warming cupboard with an approximate temperature of 40° C. for 15 min. The air head space from both syringes was then collected in two separate empty 50 ml syringes and it's NO concentration was determined by the NO chemiluminescence analyser.

The release of NO from pure incubated saliva reached a mean concentration of approximately 60 ppb. When 20 mM of nitrite was added the NO formation increased with more than 500% (396.4±138.2 vs 59.5±29.8 ppb, $p<0.005$, FIG. 2).

Example 3

Mouthwashes and NO in Exhaled Air

In order to further manipulate with the conditions in the oral cavity and perhaps influence the formation of NO from salivary nitrite different mouthwashes were introduced in the study. On a separate day, from that of the nitrate load, the ten subjects volunteered to have their NO in exhaled air measured after rinsing their mouth with distilled water, sodium bicarbonate-, ascorbic acid- and, nitrite solutions in named order. Further, a mouthwash with Chlorhexidine acetate 0.2% was included in the study.

In the first series of mouthwashes 5 baseline measurements with a breathhold were performed to obtain a reference value. In fact, all measurements in this part of the experiment were done with a breathhold, for the reasons described above. The liquid volume of all the mouthwash solutions was set to 3 cl, and the time for rinsing was set to 30 seconds. Immediately after the solutions were spat out the subjects put their lips to the mouthpiece and inhaled NO-free air, held their breath, and so on. The single-breath procedure was then repeated after 1, 2 and 3 min when it came to distilled water and sodium bicarbonate, for ascorbic acid and nitrite the single breath was repeated even after 4 and 5 min, since their effect on NO formation lasted longer. After the last measurement for each mouthwash the subjects had to wait for at least ten minutes before next measurement with a new mouthwash-solution. One single-breath was also performed before each test of a mouthwash to ensure that the NO levels roughly were back to baseline and, if not, a new measurement was made a few minutes later and the experiment was not completed until satisfactory NO values were obtained.

The composition of the different mouthwash solutions were set to concentrations that would not be toxic or harmful to the subjects and tolerable regarding taste. The sodium bicarbonate solution had a concentration of 10% (3 g/30 ml), finally, the nitrite solution had a molarity of 10 mM with pH 6.95.

At the end of this experiment a small series of dose-response rinses was carried out. regarding NO formation in relation to nitrite concentration. Three different nitrite solutions with the concentrations of 1 mM, 10 mM, and 0,1 M were used. After rinsing with each one of these solutions only one single-breath was performed. A pause of 10 min between each mouthwash was introduced and the subjects had to perform a control measurement before the next measurement.

Chlorhexidine acetate 0.2%, with pH 8.0, proved to have a longer lasting effect on the NO levels, so this experiment was performed on a separate day. To study the time lapse of the decreased NO levels measurements were made for 20 minutes after one mouthwash (30 s) with 2.5 cl chlorhexidine acetate. One single-breath measurement with a 10 s breathhold was performed immediately afterwards and after 2, 5, 10, 15 and 20 min. These measurements were compared with the mean of 5 single-breaths performed before the chlorhexidine mouthwash.

Mouthwash with distilled water gave a small decrease in exhaled NO levels of the plateau but not to the extent of statistical significance. Immediately after the mouthwash there was hardly any effect on the NO levels at all, but the reduction was more marked after 120 s ($33.4\pm5.0$ vs $41.1\pm3.3$ pmol/s, $p<0.05$). Even the peak concentration were at first hardly affected by the water but also here a certain but not significant decrease was observed after 120 s ($39.1\pm58.4$ vs $497.6\pm52.7$ ppb, $p<0.05$) (FIG. 3a).

The sodium bicarbonate was then more efficient in cutting the plateau levels. Exhaled NO was significantly reduced just after the mouthwash ($31.3\pm3.1$ pmol/s, $p<0.01$) (FIG. 3b). After 60 s the release rates of NO were still significantly low compared to baseline ($31.0\pm3,4$ pmol/s, $p<0.05$), but at 120 s the effect was slightly impaired ($34.4\pm3.6$ pmol/s, $p<0.05$). The peak levels were also significantly reduced immediately after the mouthwash ($309.2\pm43.0$ ppb, $p<0.01$), but the significance was gone already after 60 s.

The mouthwash performed with sodium bicarbonate 180 min after the nitrate load gave and even larger decrease; the plateau was here reduced with more than 30% ($36.2\pm4.2$ vs $52.7\pm4.8$ pmol/s, $p<0.05$).

Rinsing the mouth with ascorbic acid proved to give a great but short-lasting increase of NO in exhaled air. Plateau levels increased with almost 300%, compared to baseline, immediately after the mouthwash ($155.0\pm27.6$ pmol/s, $p<0.01$), but were back to normal after 120 s. The effect on the peak concentrations lasted up to 180 s and the immediate increase was around 400% ($2482.5\pm601.9$ ppb, $p<0.001$) (FIG. 4a).

The nitrite solution gave elevated NO measurements of both the plateau and the peak that would last even beyond 240 s after the mouthwash Both plateau and peak levels came to a maximum after 60 s (plateau: $225.2\pm44.0$ pmol/s, $p<0.001$; peak: $2812.1\pm622.1$ ppb, $p<0.001$) (FIG. 4b).

The concentration of the nitrite solution also proved to have an affect on the NO formation. Mouthwash with the 1 mM mixture gave a small but not significant increase of the plateau levels ($55.0\pm8.7$ pmol/s, $p<0.05$ while the 0.1 M solution gave more than a 40-fold increase compared to baseline ($1791.8\pm404.8$ pmol/s, $p<0.001$).

The antibacterial mouthwash of chlorhexidine acetate was more efficient than sodium bicarbonate in decreasing the NO levels and the effect was also more long-lasting. The immediate decrease was almost 30% compared to baseline levels ($24.1\pm3.5$ vs $33.9\pm2.9$ pmol/s, $p<0.05$, FIG. 5a). The mean values for NO excretion were lower than the baseline levels for as long as 20 min after the mouthwash, but the statistical significance for the following measurements varied due to a considerable inter-individual spread.

Example 4

Nitrate Loading and Chlorhexidine Mouthwash

In addition to the mouthwash with sodium bicarbonate after nitrite loading, the effects of chlorhexidine was studied at a stage when one could expect larger amounts of nitrite in the saliva. This was also done in a separate experiment, on a separate day, not to interfere with the results of the original nitrate loading study. Five single-breaths with a breathhold were carried out to obtain a reliable baseline. Thereafter a load of 400 mg potassium nitrate was ingested, as described above. However, to facilitate this experiment for the subjects there was no demand for fasting. Five additional single-breaths were performed 90 min later—to get representative mean values of NO after nitrate ingestion. The subjects then rinsed their mouths with 2.5 cl chlorhexidine acetate 0.2% for 30 s and performed a NO measurement immediately afterwards. The single-breath procedure was also repeated 2, 5, 10, 20 and 30 min after the mouthwash.

The mean values for NO release 90 min after the nitrate load showed an almost 2-fold increase compared to control levels ($60.8\pm6.4$ vs $34.8\pm4.2$ pmol/s, $p<0.005$). Mouthwash with chlorhexidine acetate gave at this point an immediate reduction of the NO levels close to 50% ($60.8\pm6.4$ vs $33.9\pm4.3$ pmol/s, $p<0.005$, FIG. 5b). The NO excretion also remained significantly reduced up to 30 min after the mouthwash, at every point of measurement except one, though these values were never as low as the one following directly upon rinsing, see FIG. 5b.

Experimental Part Added During the Priority Year

Example 5

Mouthwash Trials

Experimental protocol: Exhaled NO was measured at an exhalation flow rate of 100 ml/s and the NO output was calculated. Measurements were repeated 3 times at each time point and the median value was used. After baseline measurements, the test subjects (n=3) were asked to rinse their mouth with 25 ml of different solutions during 30 s whereafter the solution was spat out All solutions were made up in distilled water. Exhaled NO measurements were repeated directly after, and 5, 15 and 30 min after the mouthwash procedure. Results are given as mean relative changes in NO output compared to baseline measurements.

TABLE 1

The influence of different mouthwash compositions on NO output

| Composition | Effect |
|---|---|
| Distilled water: | −1% at 0 min |
| 1% Tween-20 ®: | −9% at 0 min |
| | −6% at 5 min |
| 0.2% chlorhexidine (pH = 8.0): | −14% at 0 min |
| | −11% at 5 min |
| | −5% at 15 min |
| | −10% at 30 min |
| 0.2% chlorhexidine + 1% Tween-20 ®: | −10% at 0 min |
| | −12% at 5 min |
| | −6% at 15 min |
| | −9% at 30 min |
| 10% NaHCO$_3$ (1.23 M, pH = 8.2): | −7% at 0 min |
| | −5% at 5 min |
| | −8% at 15 min |
| | −8% at 30 min |
| 10% NaHCO$_3$ + 1% Tween-20 ®: | −17% at 0 min |
| | −22% at 5 min |
| | −18% at 15 min |
| | −15% at 30 min |
| Tribonat ® (0.16 M NaHCO3, 0.3 M Trometamol, pH = 8.0) | −9% at 0 min |
| | −5% at 5 min |
| | −2% at 15 min |
| | +5% at 30 min |
| Tribonat ® + 1% Tween-20 ®: | −12% at 0 min |
| | −14% at 5 min |
| | −7% at 15 min |
| | +6% at 30 min |

Solutions of 1% H$_2$O$_2$ (pH=8.0), 70 mg sodium percarbonate+0.2 mg CuSO$_4$ (=Ascoxal without ascorbic acid), and 100 mg FeSO$_4$ (pH=5.0) were also tested. They all resulted in increased NO output.

Distilled water had no effect, whereas 1% Tween-20® resulted in a slight reduction of exhaled NO, indicating that the physical rinsing per se can reduce exhaled NO if a surfactant is added. This probably helps to rinse deeper down in the crypts on the base of the tongue. A surprising effect of Tween-20® was seen when used together with the buffering solutions (10% NaHCO$_3$ and Tribonat®), but not when added to chlorhexidine. The initial effect of chlorhexidine (0–15 min) might be due to the alkaline pH of this solution, but the buffering capacity is probably very poor compared to 10% NaHCO$_3$ and Tribonat®. This might explain why Tween-20® did not enhance the early effect of chlorhexidine. Interestingly, exhaled NO start to decrease further at 30 min after chlorhexidine. This might be due to the antibacterial effect of this compound. Another finding is that there seems to be a rebound effect 30 min after Tribonat® which is not seen at 30 min after 10% NaHCO$_3$. This could be due to the higher concentration of HCO$_3$-(about 8-fold) in the latter solution. Maybe a rebound effect is always seen when the buffering effect disappears.

The use of oxidizing agents like H$_2$O$_2$ or sodium percarbonate did not seem to work in the right direction. This may be due to chemistry that we do not understand or, possibly, that the bacteria get activated by H$_2$O$_2$. This is supported by the fact that the increase in exhaled NO was slightly delayed (peak at 15 min). The FeSO$_4$ solution did not reduce exhaled NO either in this trial. This could partly be due to the acidic pH of this solution. Thus it seems that alkaline buffering solutions with high ionic concentration together with a surfactant is the best Iternative to date.

Example 6

Presence of iNOS in Gingival Tissue

Human gingival biopsy specimens were snap-frozen and freeze-sectioned in a cryostat. Sections were stained using a polyclonal antibody specific for human inducible nitric oxide synthase (iNOS) and a secondary antibody conjugated with a fluorescence marker. Staning was evaluated in a Zeiss Axiophot fluorescence microscope and a dense staining was noted in the epithelal cell layer of the gingival mucosa This indicates a marked expression of iNOS in the superficial cell layers in the oral cavity. The activity of this enzyme could be blocked by administering an unselective NO synthase inhibitor such as N-omega-nitro-L-arginine methyl ester, or an iNOS-selective inhibitor such as aminoguanidine.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims attached hereto.

What is claimed is:

1. A method for the diagnostic determination of orally exhaled nitric oxide (NO) in humans, where a production of NO in the oral cavity may constitute a disturbance on the measurement of the level of NO, the method comprising temporarily lowering or inhibiting NO production in the oral cavity prior to the measurement of orally exhaled NO and measuring the level of NO within orally exhaled air.

2. A method according to claim 1, wherein the step of temporarily lowering or inhibiting the NO production in the oral cavity comprises administering a composition comprising an anti-bacterial agent, an oxidizing agent, an agent capable of raising the pH, or mixtures thereof prior to the measurement of orally exhaled NO.

3. A method according to claim 2, wherein the process of administrating said composition comprises mechanical cleaning of the teeth, gums and tongue.

4. A method according to claim 2, wherein said composition further includes a nitrate reductase inhibitor.

5. A method according to claim 2, comprising administering the composition in the form of a gel or paste with the aid of a brush.

6. A method according to claim 2, comprising administering the composition in the form of a gargling solution, and maintaining the solution agitated in the mouth sufficiently long for active ingredients therein to exert their influence.

7. A method according to claim 2, comprising spraying or nebulizing the composition into the oral cavity.

8. Method for the inhibition or neutralization of NO production in the oral cavity prior to diagnostic determination of orally exhaled NO, comprising administration of an aqueous bicarbonate solution buffered to a pH of about 8 or above.

9. Method for the inhibition or neutralization of NO production in the oral cavity prior to diagnostic determination of orally exhaled NO, comprising administration of an aqueous bicarbonate solution buffered to a pH of about 8 or above, and containing a surfactant.

\* \* \* \* \*